(12) United States Patent
Lathers et al.

(10) Patent No.: US 11,903,611 B2
(45) Date of Patent: Feb. 20, 2024

(54) ACTIVE SURGICAL ACCESS PORT FILTRATION FITTINGS

(71) Applicant: Conmed Corporation, Utica, NY (US)

(72) Inventors: Steven Lathers, Littleton, CO (US); Mahesh Krishnamoorthy, Parker, CO (US)

(73) Assignee: Conmed Corporation, Largo, FL (US)

( * ) Notice: Subject to any disclaimer, the term of this patent is extended or adjusted under 35 U.S.C. 154(b) by 313 days.

(21) Appl. No.: 17/308,255

(22) Filed: May 5, 2021

(65) Prior Publication Data

US 2022/0354536 A1 Nov. 10, 2022

(51) Int. Cl.
*A61B 17/34* (2006.01)

(52) U.S. Cl.
CPC ...... *A61B 17/3423* (2013.01); *A61B 17/3474* (2013.01); *A61B 2217/005* (2013.01)

(58) Field of Classification Search
CPC ............ A61B 17/3423; A61B 17/3474; A61B 2217/005
USPC .................................................. 600/201–245
See application file for complete search history.

(56) References Cited

U.S. PATENT DOCUMENTS

| | | |
|---|---|---|
| 5,722,962 A | 3/1998 | Garcia |
| 6,685,665 B2 | 2/2004 | Booth et al. |
| 10,492,827 B1 | 12/2019 | Velez-Cruz |
| 2009/0137943 A1 | 5/2009 | Stearns et al. |
| 2012/0283518 A1* | 11/2012 | Hart .................... A61B 17/3462 600/207 |
| 2018/0228510 A1* | 8/2018 | Holsten ............. B01D 46/0097 |
| 2019/0388631 A1* | 12/2019 | Silver ................... B01D 46/10 |
| 2021/0267639 A1 | 9/2021 | Fischer et al. |

FOREIGN PATENT DOCUMENTS

| | | |
|---|---|---|
| CN | 211433579 U | 9/2020 |
| KR | 101704903 B1 | 2/2017 |
| WO | 2020036497 A1 | 2/2020 |
| WO | 2021191885 A2 | 9/2021 |

OTHER PUBLICATIONS

PCT International Search Report and Written Opinion dated Jun. 7, 2022, issued during the prosecution of PCT International Patent Application No. PCT/US2022/016467.
PCT International Search Report and Written Opinion dated May 31, 2022, issued during prosecution of PCT International Patent Application No. PCT/US2022/016470.

\* cited by examiner

*Primary Examiner* — Eduardo C Robert
*Assistant Examiner* — Tara Rose E Carter
(74) *Attorney, Agent, or Firm* — Locke Lord LLP; Scott D. Wofsy

(57) ABSTRACT

A cap for a trocar assembly includes a housing configured to be removably attached to a proximal portion of a trocar. The housing defines an access port opening therethrough configured to be aligned for passage of a surgical instrument through the access port opening and into a main access port of the trocar. The housing defines at least one siphon opening for siphoning particles from the proximal portion of the trocar for filtration.

13 Claims, 5 Drawing Sheets

ACTIVE SURGICAL ACCESS PORT FILTRATION FITTINGS

BACKGROUND

1. Field

The present disclosure relates to active filtration, and more particularly to active filtration for surgical access ports such as used with insufflation systems.

2. Description of Related Art

Some surgical access ports are designed as open, valveless trocars with gas pressure barriers to prevent the loss of pneumoperitoneum. AirSeal® Access Ports as part of AirSeal® iFS insufflation management systems available from ConMed Corporation of Utica, New York can be introduced to a patient's surgical site during an insufflation procedure. Sometimes surgeons use AirSeal® iFS insufflation management systems in procedures where the AirSeal® Access Port is not used for access to the surgical site, e.g. when no surgical instruments are inserted through the trocar of the AirSeal® Access Port during in the procedure. In this scenario, the AirSeal® iFS insufflation management system provides the insufflation for the procedure. The AirSeal® System provides for stable pneumoperitoneum, and can also provide for smoke evacuation.

Regardless of the type of surgical access port used, due to the open nature of some access port designs, when there is no instrument passing through an access port there is an opportunity for particles to be emitted from inside a patient, through the access port opening, and into the operating room air. This can allow for unwanted or harmful particles to move from the intraabdominal cavity or other surgical site to the operating room where surgical staff/employees are present. This could include gasses or even pathogens that are harmful to the surgical staff/employees, who would have to rely on their PPE (personal protective equipment) for protection.

The conventional techniques have been considered satisfactory for their intended purpose. However, there is an ever present need for improved systems and methods for preventing unwanted or harmful particles from entering the operating room air through surgical access ports. This disclosure provides a solution for this need.

SUMMARY

A cap for a trocar assembly includes a housing configured to be removably attached to a proximal portion of a trocar. The housing defines an access port opening therethrough configured to be aligned for passage of a surgical instrument through the access port opening and into a main access port of the trocar. The housing defines a siphon opening for siphoning particles from the proximal portion of the trocar for filtration.

A plenum can be defined in the cap radially outward from the access port opening with a plenum wall separating between the plenum and the access port opening. The siphon opening can be in fluid communication with the plenum to siphon particles out of the plenum. At least one port can be defined through the plenum wall for fluid communication from the access port opening into the plenum. A tube set can be included having a siphon tube connected to the siphon opening.

The siphon tube can connect for fluid communication between the housing and an external filter unit. The external filter unit can house a filter medium spanning a flow passage through the external filter unit for filtration of flow through the flow passage. The external filter unit can include an outlet tube for connecting to an insufflator for active filtration.

It is also contemplated that the tube set can include an insufflation line and a smoke evacuation line, each connecting between a cartridge and a multiport connector. The cartridge can be configured to connect the tube set to an insufflator. The multiport connector can be configured to connect the insufflation line and the smoke evacuation line to a trocar for insufflation and smoke evacuation. The siphon tube can connect to the smoke evacuation line for active filtration of particles from the trocar by the filter medium. The cartridge can include an ultra-low particulate air (ULPA) filter medium in fluid communication with the siphon line for filtration of particles from the trocar.

The housing can define an inlet opening in fluid communication with the access port opening, wherein the inlet opening is configured to engage the trocar. A seal can extend circumferentially around the inlet opening. The seal can be configured to engage the proximal portion of the trocar to drive all flow into and out of a main lumen of the trocar through the inlet opening. A seal seat can be defined about the inlet opening of the housing. The seal can be seated in the seal seat.

A distal end of the housing can include at least one inward extending latch member configured to engage a respective rim or detent of the trocar to maintain engagement of the housing to the trocar. It is also contemplated that the distal end of the housing can include a plurality of circumferentially spaced apart, inward extending latch members configured to engage a respective rim or detent of the trocar to maintain engagement of the housing to the trocar.

A trocar assembly includes a trocar. The trocar includes an elongated tubular member extending between a distal end configured to be inserted into a surgical site and a proximal portion including a trocar housing configured for introduction of surgical instruments into the tubular member. The trocar housing includes at least one latch receptacle. A cap as described above is included, wherein the housing of the cap is attached to the proximal portion of the trocar. A kit includes a trocar as described above, and a cap as described above, wherein the trocar and cap are attached or separate from one another in the kit.

A method includes regulating insufflation of a surgical site with a trocar introduced into the surgical site. The method includes siphoning fluid that vents out of the surgical site through the trocar into a tube set, thereby diverting the fluid from reaching a space external of the surgical site.

The method can include capturing liquid droplets, solid particulate, and/or gas from the fluid in a filter medium in a flow path of the fluid. The filter medium can be in a fluid circuit connecting between the trocar and an insufflator regulating insufflation with the trocar and/or conducting smoke evacuation through the trocar. The filter medium can be within an insufflator regulating insufflation with the trocar and/or conducting smoke evacuation through the trocar. The method can include evacuating smoke from the surgical site through the trocar and/or regulating stable pneumoperitoneum using the trocar.

The trocar can be a first access port, and the method can include accessing the surgical site through second access port. Accessing the surgical site through the second access port can include accessing the surgical site without accessing the surgical site through the first access port.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
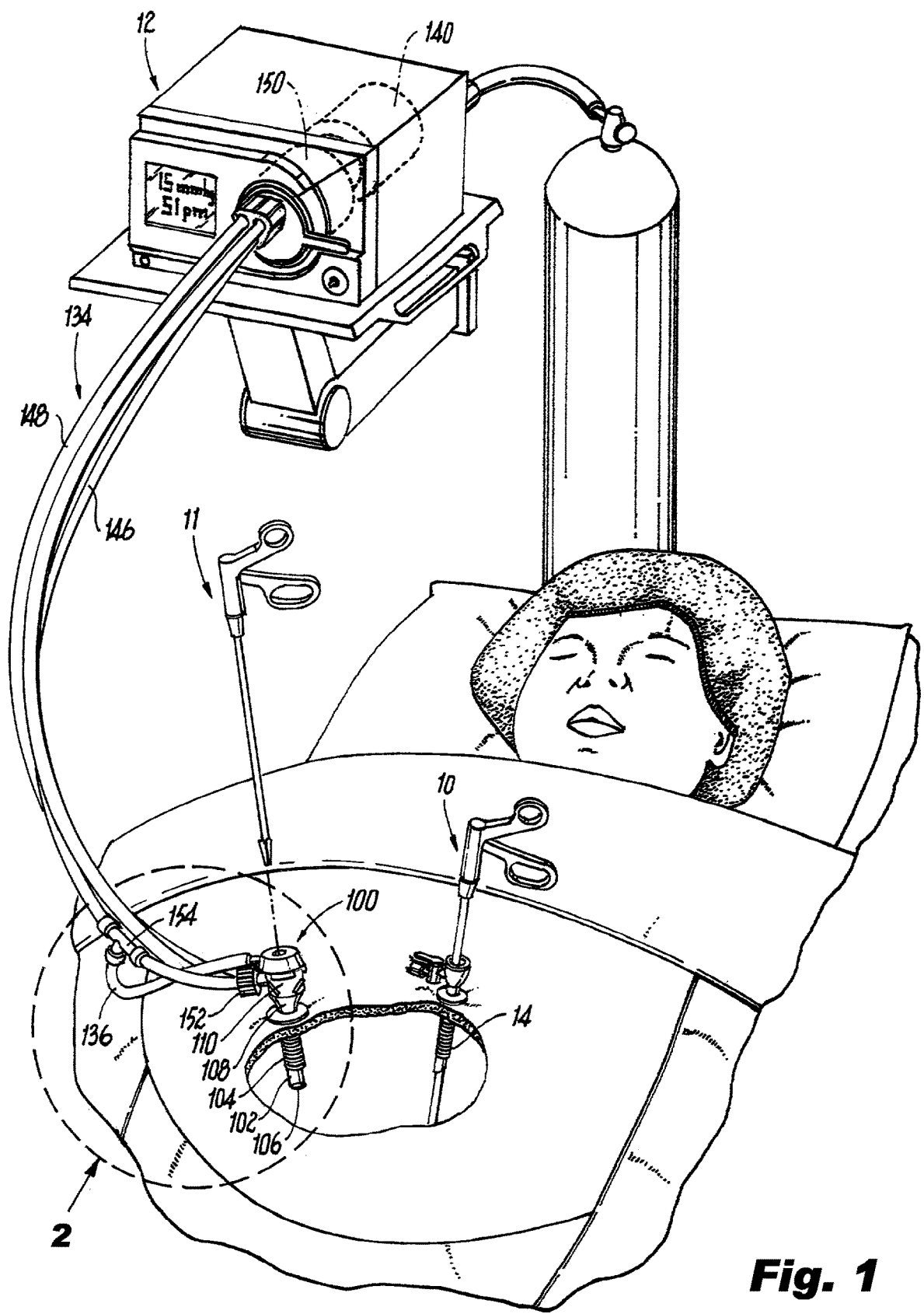
FIG. 1 is a schematic perspective view of an embodiment of a trocar assembly constructed in accordance with the present disclosure, showing the trocar assembly in situ during a procedure on a patient using insufflation.

Reference will now be made to the drawings wherein like reference numerals identify similar structural features or aspects of the subject disclosure. For purposes of explanation and illustration, and not limitation, a partial view of an embodiment of a trocar assembly in accordance with the disclosure is shown in FIG. 1 and is designated generally by reference character 100. Other embodiments of systems in accordance with the disclosure, or aspects thereof, are provided in FIGS. 2-7, as will be described. The systems and methods described herein can be used to provide active filtration to prevent particles from within a pneumoperitoneum from entering the operating room air without impeding the performance or effectiveness of the insufflation or stable pneumoperitoneum.

The trocar assembly 100 includes a trocar 102. The trocar includes an elongated tubular member 104 extending between a distal end 106 configured to be inserted into a surgical site and a proximal portion 108 including a trocar housing 110 configured for introduction of surgical instruments, e.g. surgical instrument 11, into the tubular member 104.

Figures 2, 3:
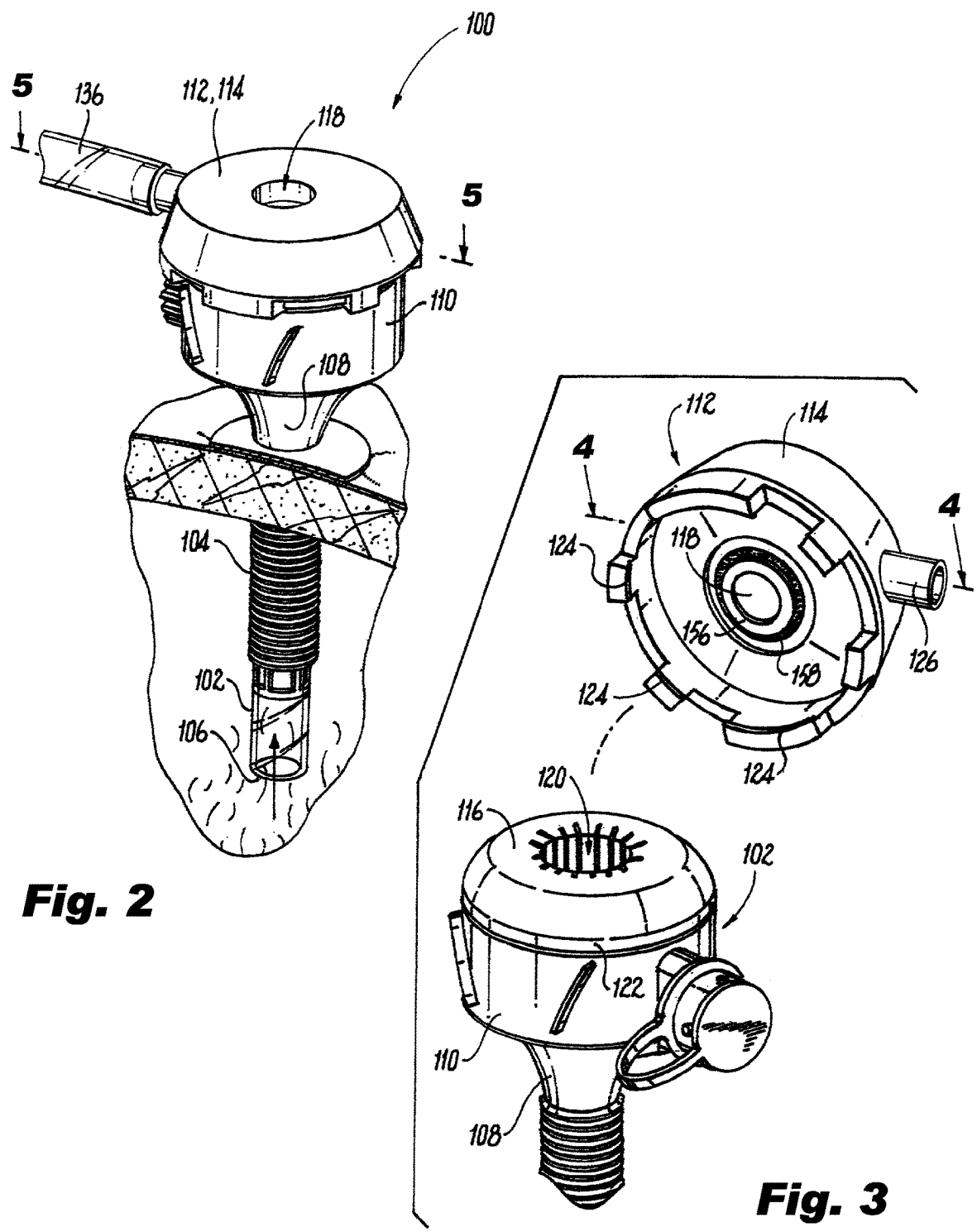
FIG. 2 is a perspective view of the trocar assembly of FIG. 1, showing the passive filtration cap in place on the trocar.
FIG. 3 is an exploded perspective view of the trocar assembly of FIG. 2, showing the cap removed from the trocar.

With reference now to FIG. 2, the assembly 100 includes a cap 112. The cap 112 includes a cap housing 114 configured to be removably attached to a proximal portion 108 of the trocar 102, e.g. to a proximal end 116 of the trocar housing 110. The housing 114 defines an access port opening 118 therethrough configured to be aligned for passage of a surgical instrument, e.g. surgical instrument 11 of FIG. 1, through the access port opening 118 and into a main access port 120 of the trocar 102, which is labeled in FIG. 3.

With continued reference to FIG. 3, the trocar housing 110 includes at least one latch receptacle 122 in the form of a rim or detent. A distal end of the housing 114 includes a plurality of circumferentially spaced apart inward extending latch members 124 configured to engage the latch receptacle 122 of the trocar 102 to maintain engagement of the cap 112 to the trocar 102. The housing 114 defines a siphon opening 126 for siphoning particles from the proximal portion 108 of the trocar 102 for filtration.

Figure 4:
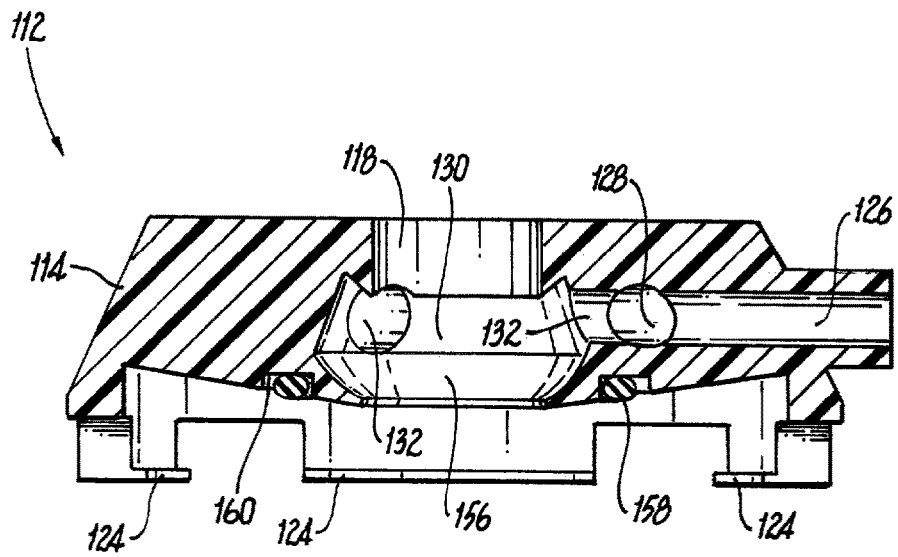
FIG. 4 is a cross-sectional side elevation view of the cap of FIG. 3, showing the access port opening and the siphon opening communicating through a plenum.
Figure 5:
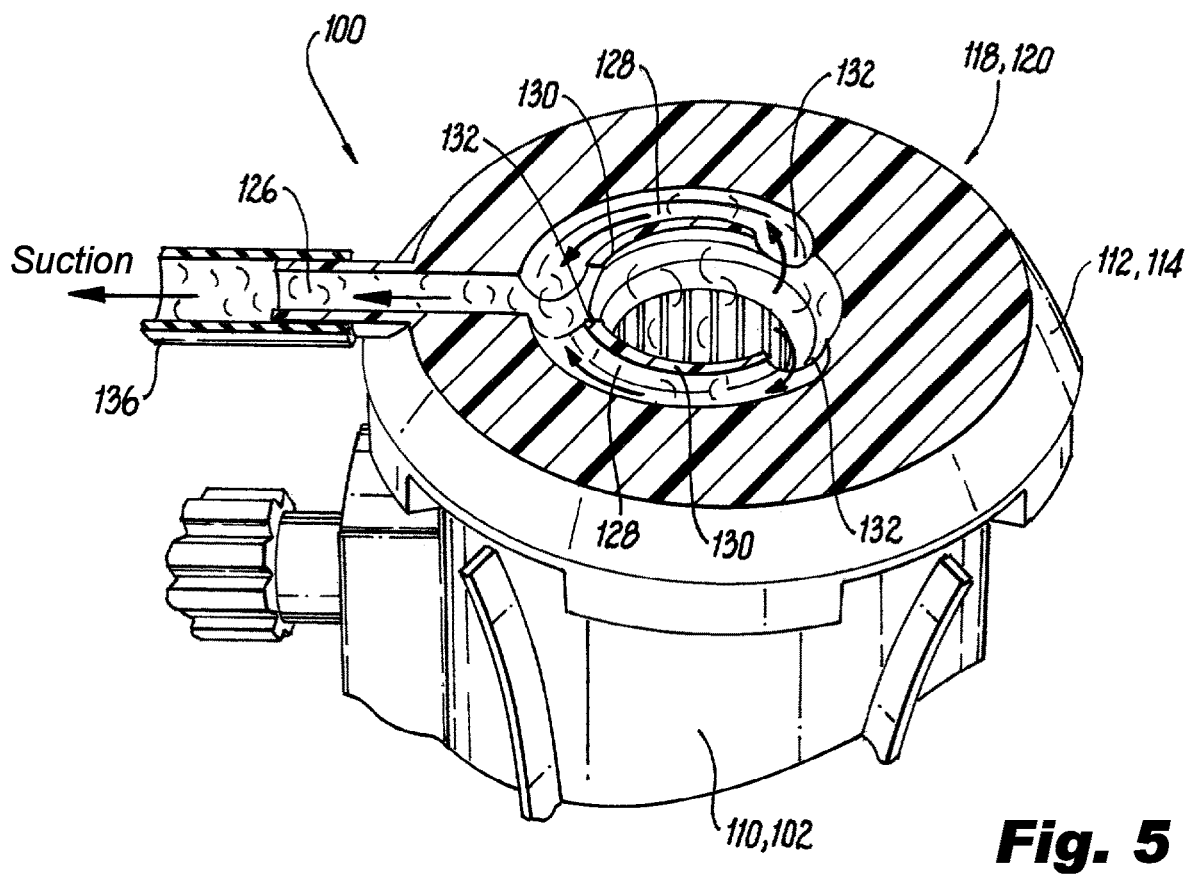
FIG. 5 is a cross-sectional perspective view of the cap of FIG. 3, showing the plenum wall separating between the access port opening and the plenum.
Figure 7:
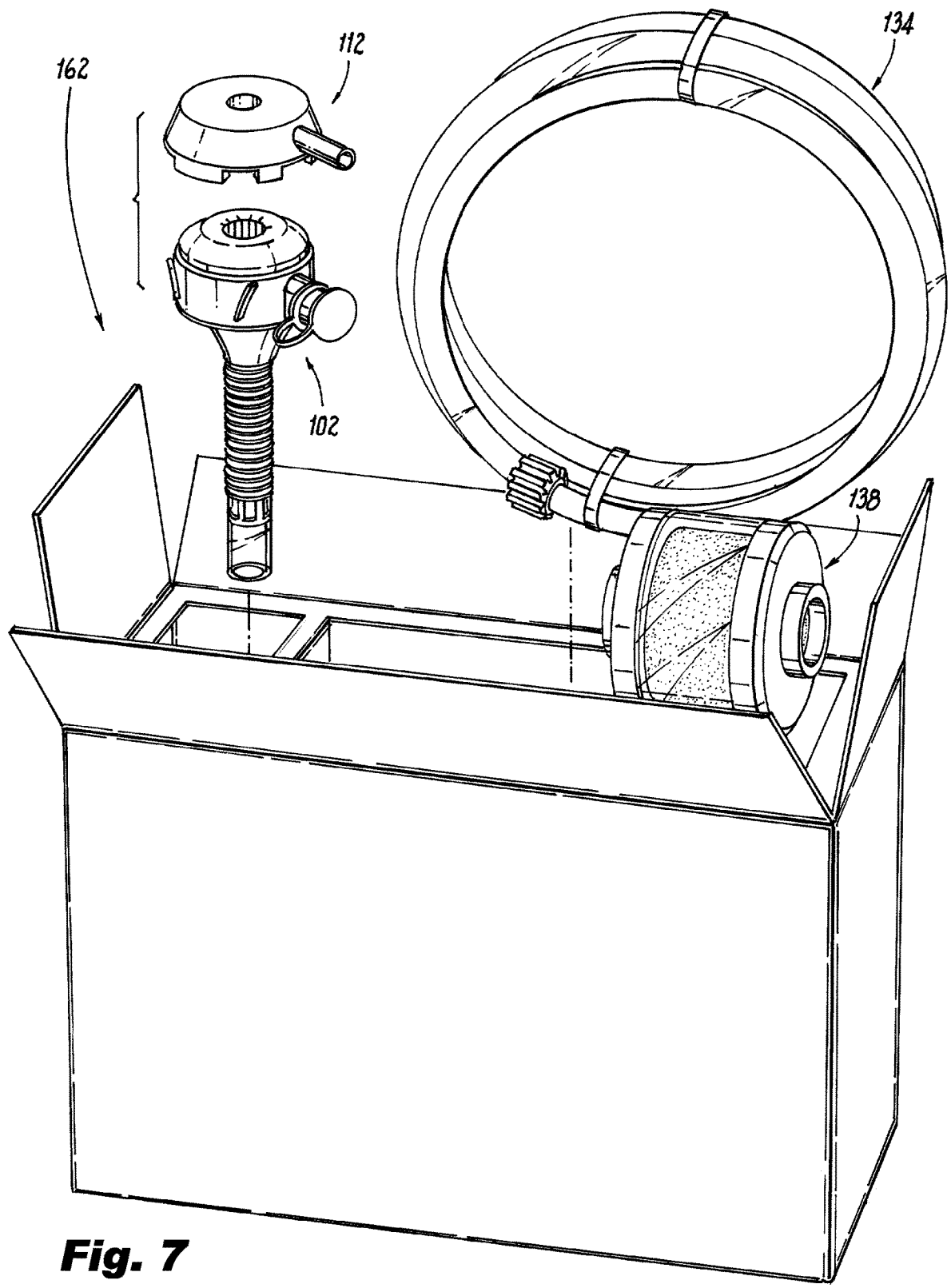
FIG. 7 is a is a perspective view of an embodiment of a kit including parts for the trocar assembly of FIG. 1.

With reference now to FIG. 4, a plenum 128 is defined in the cap 112 radially outward from the access port opening 118 with a plenum wall 130 separating between the plenum 128 and the access port opening 118. The plenum wall is shown in cross-section in FIG. 5. The siphon opening 126 is in fluid communication with the plenum 128 to siphon particles out of the plenum 128, and ultimately from the access port opening 118. At least one port 132 is defined through the plenum wall 130 for fluid communication from the access port opening 118 into the plenum 128. In FIGS. 4-5, there are three ports 132 through the plenum wall 130, however any suitable number of ports can be used without departing from the scope of this disclosure. A tube set 134 (e.g. as shown in FIG. 7) is included, having a siphon tube 136 configured to connect to the siphon opening 126 when in use.

With continued reference to FIG. 4, the cap housing 114 defines an inlet opening 156 in fluid communication with the access port opening 118, wherein the inlet opening 156 is configured to engage the trocar 102 of FIGS. 1-3. A seal 158 extends circumferentially around the inlet opening 156. The seal 158 is configured to engage the proximal end 116 of the proximal portion 108 of the trocar 102 (as labeled in FIG. 3) to drive all flow into and out of a main lumen of the trocar 102 through the inlet opening 156. A seal seat 160 is defined about the inlet opening 156, and the seal 158 is seated in the seal seat 160. It is also contemplated that in addition to or in lieu of seal 158 and seal seat 160, a polymer adhesive can be applied around the inlet opening 156 to seal with the trocar 102.

Figure 6:
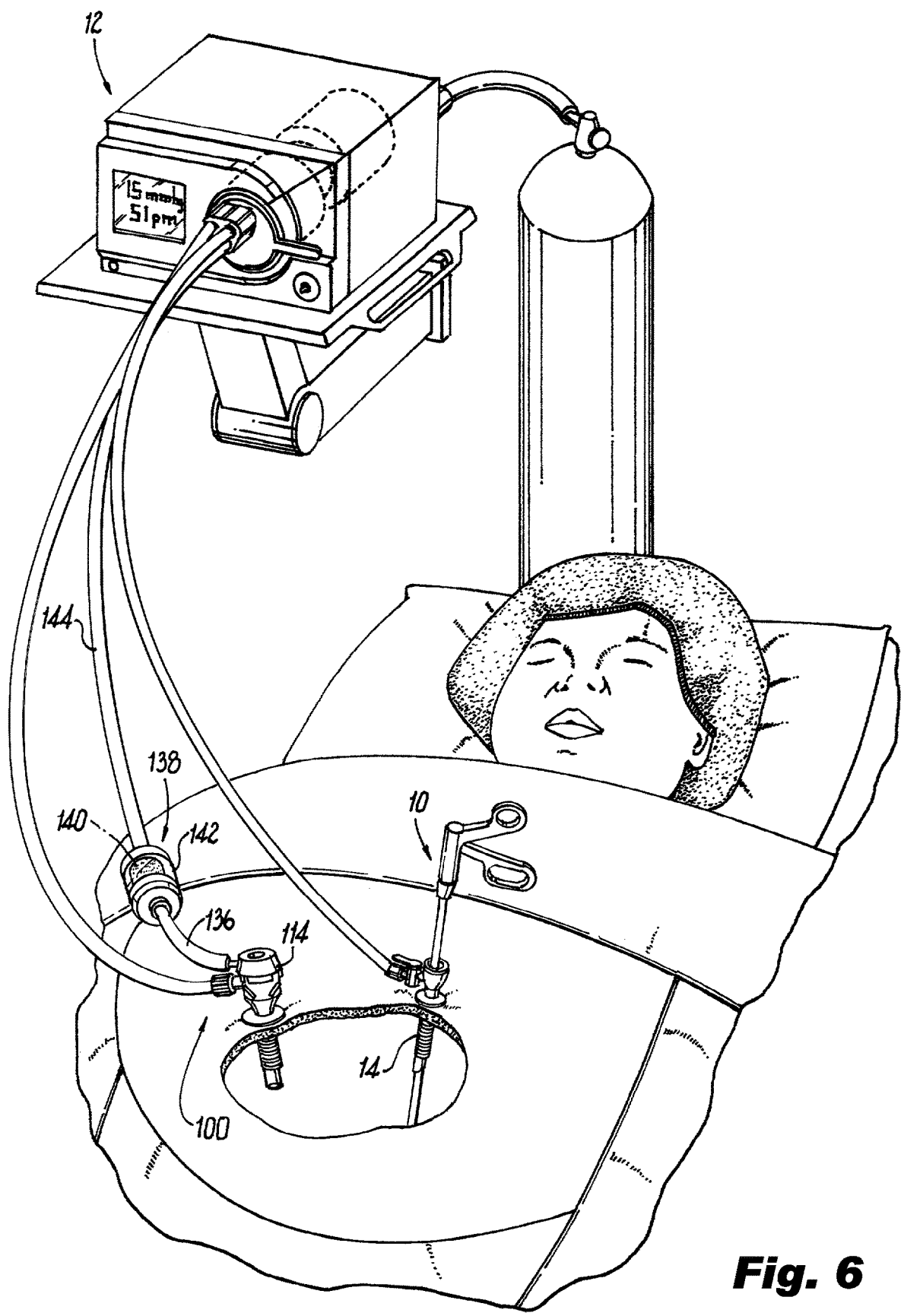
FIG. 6 is a schematic perspective view of another embodiment of a trocar assembly constructed in accordance with the present disclosure, showing the trocar assembly in situ during a procedure on a patient using insufflation, with an external filter for capture of particulate from the siphon opening.

With reference to FIG. 6, the siphon tube 136 can connect for fluid communication between the cap housing 114 and an external filter unit 138. The external filter unit 138 houses a filter medium 140, e.g., an ultra-low particulate air (ULPA) filter medium, spanning a flow passage 142 through the external filter unit 138 for filtration of flow through the flow passage 142. The external filter unit 138 includes an outlet tube 144 for connecting to an insufflator 12 for active filtration of particles from the housing 114, e.g. to reduce or prevent those particles escaping into the operating room. The outlet tube 144 can be connected to any suitable source of suction, such as a smoke evacuation system in an insufflator 12, a central surgical vacuum system, or the like.

It is also contemplated that the external filter unit 138 need not be included, for example as shown in FIG. 1, where the tube set 134 includes a pair of insufflation lines 146 and a smoke evacuation line 148, each connecting between a cartridge 150 and a multiport connector 152. The cartridge 150 is configured to connect the tube set 134 to an insufflator 12. The multiport connector 152 is configured to connect the insufflation lines 146 and the smoke evacuation line 148 to the trocar housing 110 of the trocar 102 for insufflation and smoke evacuation. The siphon tube 136 connects to the smoke evacuation line 148, e.g. with a y- or t-connector 154 for active filtration of particles from the trocar 102 by the filter medium, which in this case can be in the cartridge 150, or in the insufflator 12. The siphon line 136 can instead be connected to any suitable source of suction.

With reference now to FIG. 7, a kit 162 includes a trocar 102 as described above, and a cap 112 as described above, wherein the trocar 102 and cap 112 are attached or separate from one another in the kit. It is also contemplated that the kit can include the tube set 134, and if applicable the external filter unit 138 as described above.

A method includes regulating insufflation of a surgical site with a trocar, e.g. trocar 102, introduced into the surgical site. The method includes siphoning fluid that vents out of the surgical site through the trocar into a tube set, e.g. tube set 134, thereby diverting the fluid from reaching a space external of the surgical site.

This can include capturing liquid droplets, solid particulate, and/or gas from the fluid in a filter medium, e.g. filter medium 140, in a flow path, e.g. flow passage 142, of the fluid. The filter medium is in a fluid circuit connecting between the trocar and an insufflator, e.g. insufflator 112, regulating insufflation with the trocar and/or conducting smoke evacuation through the trocar. The filter medium can be within an insufflator regulating insufflation with the trocar and/or conducting smoke evacuation through the trocar, as shown in FIG. 1, or in an external filter housing in the tube set, as shown in FIG. 6. The method can include evacuating smoke from the surgical site through the trocar and/or regulating stable pneumoperitoneum using the trocar. The trocar 102 can be a first access port, and the method can include accessing the surgical site through second access port, e.g. access port 114 shown in FIGS. 1 and 6. Accessing the surgical site through the second access port can include accessing the surgical site without accessing the surgical site through the first access port, i.e. optionally a surgical instrument such as surgical instrument 10, 11 of FIGS. 1 and 6 can access the surgical site through the trocar 102 and cap 112, or through a separate access port 14, or through both. The second access port 14 can optionally be connected to an insufflation system.

The methods and systems of the present disclosure, as described above and shown in the drawings, provide for active filtration to prevent particles from within a pneumoperitoneum from entering the operating room air without impeding the performance or effectiveness of the insufflation or stable pneumoperitoneum. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A cap for a trocar assembly comprising:
a housing configured to be removably attached to a proximal portion of a trocar, wherein the housing defines an access port opening therethrough configured to be aligned for passage of a surgical instrument through the access port opening and into a main access port of the trocar, and wherein the housing defines a siphon opening for siphoning particles from the proximal portion of the trocar for filtration, wherein a plenum is defined in the housing radially outward from the access port opening with a plenum wall separating between the plenum and the access port opening, wherein the siphon opening is in fluid communication with the plenum to siphon particles out of the plenum, and wherein at least one port is defined through the plenum wall for fluid communication from the access port opening into the plenum.

2. The cap as recited in claim 1, further comprising a tube set including a siphon tube connected to the siphon opening.

3. The cap as recited in claim 2, wherein the siphon tube connects for fluid communication between the housing and an external filter unit, wherein the external filter unit houses a filter medium spanning a flow passage through the external filter unit for filtration of flow through the flow passage.

4. The cap as recited in claim 3, wherein the external filter unit includes an outlet tube for connecting to an insufflator for active filtration.

5. The cap as recited in claim 2, wherein the tube set includes an insufflation line and a smoke evacuation line, each connecting between a cartridge and a multiport connector, wherein the cartridge is configured to connect the tube set to an insufflator, wherein the multiport connector is configured to connect the insufflation line and the smoke evacuation line to a trocar for insufflation and smoke evacuation, and wherein the siphon tube connects to the smoke evacuation line for active filtration of particles from the trocar by a filter medium.

6. The cap as recited in claim 5, wherein the cartridge includes an ultra-low particulate air (ULPA) filter medium in fluid communication with the at least one siphon line for filtration of particles from the trocar.

7. The cap as recited in claim 1, wherein the housing defines an inlet opening in fluid communication with the access port opening, wherein the inlet opening is configured to engage the trocar.

8. The cap as recited in claim 7, further comprising a seal extending circumferentially around the inlet opening, wherein the seal is configured to engage the proximal portion of the trocar to drive all flow into and out of a main lumen of the trocar through the inlet opening.

9. The cap as recited in claim 8, wherein a seal seat is defined about the inlet opening of the housing, wherein the seal is seated in the seal seat.

10. The cap as recited in claim 1, wherein a distal end of the housing includes at least one inward extending latch member configured to engage a respective rim or detent of the trocar to maintain engagement of the housing to the trocar.

11. The cap as recited in claim 10, wherein the at least one inward extending latch member includes a plurality of circumferentially spaced apart, inward extending latch members.

12. A trocar assembly comprising:
a trocar including:
an elongated tubular member extending between a distal end configured to be inserted into a surgical site and a proximal portion including a trocar housing configured for introduction of surgical instruments into the tubular member, wherein the trocar housing includes at least one latch receptacle; and
a cap including:
a cap housing attached to the proximal portion of the trocar, wherein the cap housing defines an access port opening therethrough aligned for passage of a surgical instrument therethrough and into the tubular member of the trocar, wherein the cap housing defines at least one siphon opening for siphoning particles from the proximal portion of the trocar for filtration, wherein a plenum is defined in the cap housing radially outward from the access port opening with a plenum wall separating between the plenum and the access port opening, wherein the at least one siphon opening is in fluid communication with the plenum to siphon particles out of the plenum, and wherein at least one port is defined through the plenum wall for fluid communication from the access port opening into the plenum.

13. A kit comprising:

a trocar including:
  an elongated tubular member extending between a distal end configured to be inserted into a surgical site and a proximal portion including a trocar housing configured for introduction of surgical instruments into the tubular member, wherein the trocar housing includes at least one latch receptacle; and a cap including:
  a cap housing configured to be removably attached to the proximal portion of the trocar, wherein the cap housing defines an access port opening therethrough configured to be aligned for passage of a surgical instrument therethrough and into the tubular member of the trocar, wherein the cap housing defines at least one siphon opening for siphoning particles from the proximal portion of the trocar for filtration, wherein a plenum is defined in the cap housing radially outward from the access port opening with a plenum wall separating between the plenum and the access port opening, wherein the at least one siphon opening is in fluid communication with the plenum to siphon particles out of the plenum, and wherein at least one port is defined through the plenum wall for fluid communication from the access port opening into the plenum.

* * * * *